(12) United States Patent
Nakajima et al.

(10) Patent No.: US 7,056,884 B2
(45) Date of Patent: Jun. 6, 2006

(54) REDUCED FK228 AND USE THEREOF

(75) Inventors: Hidenori Nakajima, Tsukuba (JP); Akito Tanaka, Tsukuba (JP); Minoru Yoshida, Kawaguchi (JP); Sueharu Horinouchi, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 261 days.

(21) Appl. No.: 10/333,063

(22) PCT Filed: Jul. 9, 2001

(86) PCT No.: PCT/JP01/05954

§ 371 (c)(1), (2), (4) Date: Sep. 29, 2003

(87) PCT Pub. No.: WO02/06307

PCT Pub. Date: Jan. 24, 2002

(65) Prior Publication Data

US 2004/0053820 A1    Mar. 18, 2004

(30) Foreign Application Priority Data

Jul. 17, 2000 (JP) .............................. 2000-216584

(51) Int. Cl.
*A61K 38/00* (2006.01)
*C07K 16/00* (2006.01)

(52) U.S. Cl. .................. 514/10; 530/317; 530/323
(58) Field of Classification Search .................. 514/10; 530/317, 323
See application file for complete search history.

(56) References Cited

U.S. PATENT DOCUMENTS 4,977,138 A * 12/1990 Okuhara et al. ............... 514/10
5,847,074 A * 12/1998 Yamasaki et al. ............ 530/325

FOREIGN PATENT DOCUMENTS

EP       352646       1/1990
WO       95/7293      3/1995

OTHER PUBLICATIONS

Khan W. Li et al.: "Total synthesis of the antitumor depsipeptide FR-901,228" J. Am. Chem. Soc., vol. 118, pp. 7237-7238 1996.
U.S. Appl. No. 11/064,292, filed Feb. 24, 2005, Naoe et al.
U.S. Appl. No. 10/333,063, filed Sep. 29, 2003, Nakajima et al.

* cited by examiner

*Primary Examiner*—Deborah C. Lambkin
(74) *Attorney, Agent, or Firm*—Oblon, Spivak, McClelland, Maier & Neustadt, P.C.

(57) ABSTRACT

The present invention relates to reduced FK228 of the formula (I)

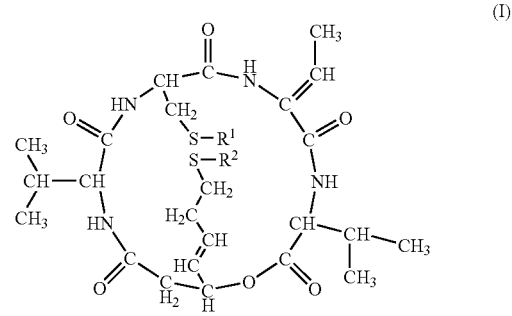

wherein $R^1$ and $R^2$ are the same or different and each is a hydrogen atom or a thiol-protecting group, or a salt thereof, and a histone deacetylase inhibitor containing this compound, an expression potentiator and a reactivation promoter of a transgene, and pharmaceutical agents containing them as active ingredients. The reduced FK228 or a salt thereof has a strong histone deacetylase inhibitory activity and this compound can be used for the prophylaxis or treatment of various diseases, in which histone deacetylation is involved, and for the gene therapy of such diseases.

6 Claims, No Drawings

REDUCED FK228 AND USE THEREOF

CROSS REFERENCES TO RELATED APPLICATIONS

This application is a 371 of International Patent Application No. PCT/JP01/05954, filed on Jul. 9, 2001, and claims priority to Japanese Patent Application No. 2000-216584, filed on Jul. 17, 2000

TECHNICAL FIELD

The present invention relates to a compound having a histone deacetylase inhibitory activity and use thereof.

BACKGROUND ART

Histone deacetylase is a metallodeacetylation enzyme having Zn in an active center (M. S. Finnin et al., Nature 401, 188–193 (1999)). This enzyme is considered to change affinity of various acetylated histones for DNA. The direct biological phenomenon brought about thereby is a structural change of chromatin. The minimum unit of chromatin structure is a nucleosome wherein 146 bp DNA is wound 1.8 times counterclockwise around a histone octamer (H2A, H2B, H3 and H4, each 2 molecules, core histone). The core histone stabilizes nucleosome structure by interaction of the positive charge of the N-terminal of each histone protein with DNA. The acetylation of histone is controlled by the balance between acetylation reaction, in which histone acetyltransferase is involved, and deacetylation, in which histone deacetylase is involved. The acetylation of histone occurs in a lysin residue of the N-terminal of histone protein that is evolutionally well preserved. Consequently, it is considered that the core histone protein loses electric charge of N-terminal, the interaction with DNA is attenuated and the nucleosomal structure becomes unstable. Therefore, deacetylation of histone is considered to bring about the opposite, or stabilization of nucleosomal structure. However, there are much to be clarified with regard to the degree of change of chromatin structure due to acetylation and the relationship thereof with the secondarily derived transcriptional control and the like.

On the other hand, a compound represented by the formula

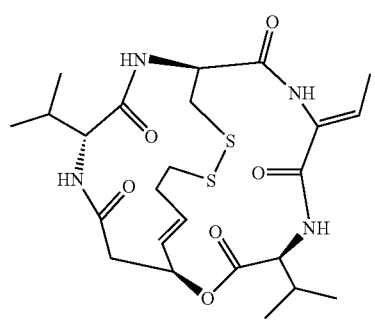

(IV)

(hereinafter to be also referred to as FR901228 substance) has been reported to derive a potent antitumor activity by selectively inhibiting histone deacetylase. Moreover, this substance causes high histone acetylation in treated cells, as a result of which it derives transcriptional control activity for various genes, cell cycle inhibitory activity and apoptosis inhibitory activity (JP-B-7-64872, H. Nakajima et al., Exp. Cell Res. 241, 126–166 (1998)). While there have heretofore been various reports on histone deacetylase inhibitors derived from naturally occurring substances, the FR901228 substance is a first pharmaceutical agent that has connected histone acetylation with biological phenomena expressed thereby, and whose clinical utility has been agreed on. The FR901228 substance has a disulfide bond in a molecule.

It is an object of the present invention to provide a compound having a stronger histone deacetylase inhibitory activity and a histone deacetylase inhibitor comprising the compound. Another object of the present invention is to provide use of the compound having a histone deacetylase inhibitory activity as a pharmaceutical agent.

DISCLOSURE OF THE INVENTION

As a result of the intensive studies done by the present inventors in an attempt to achieve the above-mentioned objects, it has been found that, by reducing the disulfide bond of the FR901228 substance into a thiol form, a stronger histone deacetylase inhibitory activity can be afforded, and further that this compound is useful as a pharmaceutical agent, which resulted in the completion of the present invention. Accordingly, the present invention provides the following.

(1) A compound represented by the formula (I)

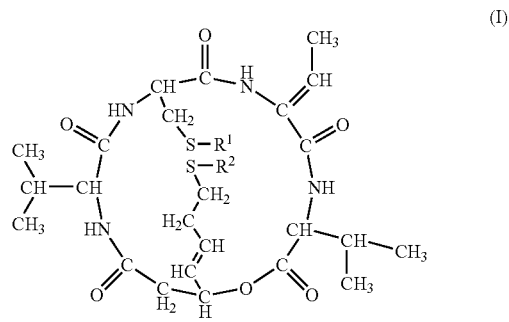

(I)

wherein $R^1$ and $R^2$ are the same or different and each is a hydrogen atom or a thiol-protecting group, or a salt thereof.

(2) The compound of the above-mentioned (1), wherein $R^1$ and $R^2$ are each a hydrogen atom, or a salt thereof.

(3) The compound of the above-mentioned (2), which is represented by the formula (II)

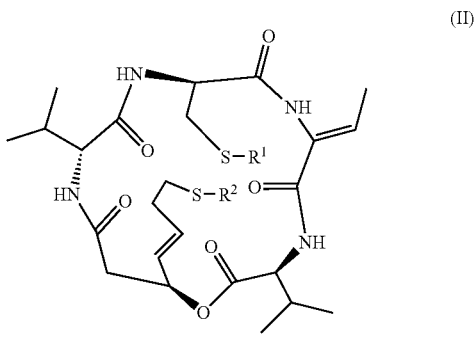

(II)

wherein R¹ and R² are each a hydrogen atom (hereinafter to be also referred to as an FR135313 substance), or a salt thereof.

(4) A production method of a compound of any of the above-mentioned (1)–(3) or a salt thereof, which comprises a step for cleaving a disulfide bond in a compound represented by the formula (III)

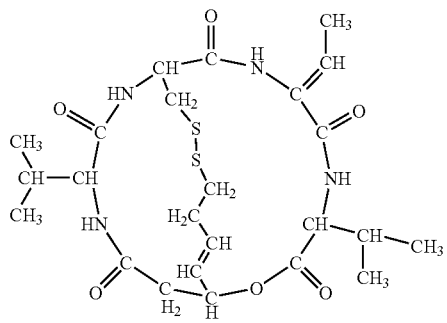

(hereinafter to be also referred to as FK228).

(5) The production method of the above-mentioned (4), wherein the compound of the formula (III) is represented by the formula (IV)

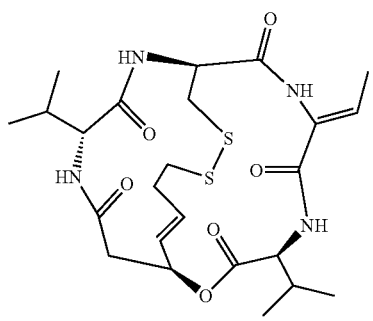

(hereinafter to be also referred to as an FR901228 substance).

(6) The production method of the above-mentioned (5), which comprises a step for culturing a bacterial strain belonging to the genus *Chromobacterium*, which is capable of producing a compound of the formula (IV), in an aqueous nutrient medium under aerobic conditions and recovering the compound, and a step for cleaving a disulfide bond in the recovered compound of the formula (IV).

(7) A histone deacetylase inhibitor comprising a compound of any of the above-mentioned (1)–(3), or a salt thereof.

(8) A pharmaceutical composition for the treatment or prophylaxis of tumor, inflammatory disorders, diabetes, diabetic complication, homozygous thalassemia, fibrosis, cirrhosis, acute promyelocytic leukemia (APL), organ transplant rejection or autoimmune disease, which comprises a compound of any of the above-mentioned (1)–(3), or a salt thereof, as an active ingredient.

(9) An expression potentiator or reactivation promoter of a transgene, which comprises a compound of any of the above-mentioned (1)–(3), or a salt thereof, as an active ingredient.

(10) The expression potentiator or reactivation promoter of a transgene of the above-mentioned (9), which is a pharmaceutical agent.

(11) The expression potentiator or reactivation promoter of a transgene of the above-mentioned (10), wherein the pharmaceutical agent is for gene therapy.

(12) A method for the treatment or prophylaxis of tumor, inflammatory disorders, diabetes, diabetic complication, homozygous thalassemia, fibrosis, cirrhosis, acute promyelocytic leukemia (APL), organ transplant rejection or autoimmune disease, which comprises administering a pharmaceutically effective amount of a compound of any of the above-mentioned (1)–(3), or a salt thereof, to patients.

(13) A method for potentiating expression of a transgene or for promoting reactivation of a transgene, which comprises administering a pharmaceutically effective amount of a compound of any of the above-mentioned (1)–(3), or a salt thereof, to patients.

(14) The method of the above-mentioned (13), wherein the administration to patients is for gene therapy.

(15) Use of a compound of any of the above-mentioned (1)–(3), or a salt thereof, for the production of a pharmaceutical composition for the treatment or prophylaxis of tumor, inflammatory disorders, diabetes, diabetic complication, homozygous thalassemia, fibrosis, cirrhosis, acute promyelocytic leukemia (APL), organ transplant rejection or autoimmune disease.

(16) Use of a compound of any of the above-mentioned (1)–(3), or a salt thereof, for the production of an expression potentiator of a transgene or a reactivation promoter of a transgene.

(17) The use of the above-mentioned (16), wherein the expression potentiator of a transgene or the reactivation promoter of a transgene is for gene therapy.

DETAILED DESCRIPTION OF THE INVENTION

The present invention provides a compound represented by the following formula(I)

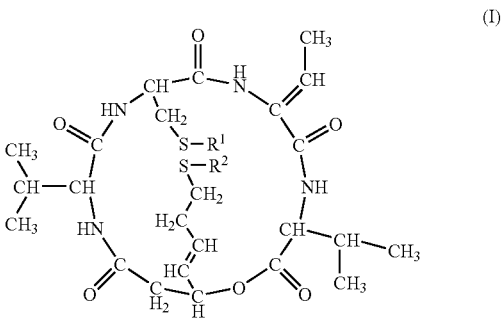

wherein R¹ and R² are the same or different and each is a hydrogen atom or a thiol-protecting group, or a salt thereof. Preferably, both R¹ and R² are hydrogen atoms, more preferably an FR135313 substance represented by the following formula

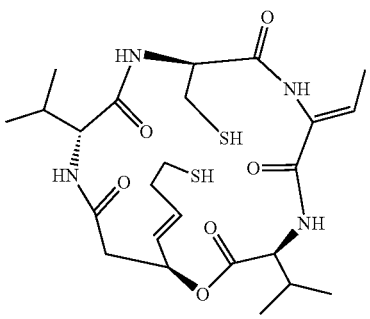

The details of the above-mentioned definitions and their preferable embodiments are given in the following.

The term "lower" used in the present specification means 1 to 6 carbon atoms, unless otherwise indicated.

In the present invention, a suitable thiol-protecting group is that generally used in this field, which is exemplified by, but not limited to, the following:

those that form thioether to protect thiol group, such as benzyl group optionally having substituents [the substituent is exemplified by lower alkoxy (e.g., methoxy etc.), acyloxy (e.g., acetoxy etc.), hydroxy, nitro and the like], picolyl, picolyl-N-oxide, anthrylmethyl, diphenylmethyl, phenyl, t-butyl, adamanthyl, acyloxymethyl (e.g., pivaloyloxymethyl, tertiary butoxycarbonyloxymethyl etc.) and the like;

those that form monothio, dithio or aminothioacetal to protect thiol group, such as lower alkoxymethyl (e.g., methoxymethyl, isobutoxymethyl etc.), tetrahydropyranyl, benzylthiomethyl, phenylthiomethyl, thiazolidine, acetamidemethyl, benzamidomethyl and the like;

those that form thioester to protect thiol group, such as tertiary butoxycarbonyl (BOC), acetyl and its derivative, benzoyl and its derivative and the like;

those that form carbamine acid thioester to protect thiol group, such as carbamoyl, phenylcarbamoyl, lower alkylcarbamoyl (e.g., methylcarbamoyl, ethylcarbamoyl etc.) and the like; and the like. More specifically, each protecting group described in PROTECTIVE GROUPS IN ORGANIC SYNTHESIS, Second Edition, T. W. Greene, P. G. M. Wuts WILEY-INTERSCIENCE is preferably used.

The above-mentioned compound of the formula (I) may have stereoisomer such as optical isomer or geometric isomer based on an asymmetric carbon atom and a double bond, all of which isomers and mixtures thereof are also encompassed in the present invention. Moreover, the compound of the formula (I) can form a salt, which is also encompassed in the present invention. The salt is a biologically acceptable salt that is generally non-toxic, and is exemplified by salts with base and acid addition salts, inclusive of salts with inorganic base such as alkali metal salt (e.g., sodium salt, potassium salt and the like), alkaline earth metal salt (e.g., calcium salt, magnesium salt and the like), ammonium salt, salts with organic base such as organic amine salt (e.g., triethylamine salt, diisopropylethylamine salt, pyridine salt, picoline salt, ethanolamine salt, triethanolamine salt, dicyclohexylamine salt, N',N'-dibenzylethylenediamine salt and the like), inorganic acid addition salt (e.g., hydrochloride, hydrobromide, sulfate, phosphate and the like), organic carboxylic acid or sulfonic acid addition salt (e.g., formate, acetate, trifluoroacetate, maleate, tartrate, fumarate, methanesulfonate, benzenesulfonate, toluenesulfonate and the like), salt with basic or acidic amino acid (e.g., arginine, aspartic acid, glutamic acid and the like), and the like. Further, solvate compounds (e.g., inclusion compound such as hydrate and the like) thereof are also encompassed in the present invention.

In the compound of the formula (I) of the present invention, the disulfide bond of the compound (FK228) represented by the formula (III) is cleaved, and can be referred to as reduced FK228, or FK228 thiol form (hereinafter the series of the compounds of the present invention are also generally referred to as an FK228 thiol form).

The present invention also provides a production method of the FK228 thiol form of the present invention. The production method of the FK228 thiol form of the present invention characteristically includes a step for cleaving the disulfide bond of FK228. The cleavage of this bond can be conducted by a method known in this field to the degree that does not adversely influence the histone deacetylase inhibitory activity of the obtained FK228 thiol form, or by a method modified as necessary.

More specifically, the cleavage of the disulfide bond is achieved using a thiol compound generally used for a reduction treatment of a protein generally having a disulfide bond, such as mercaptoethanol, thioglycol acid, 2-mercaptoethylamine, benzenethiol, parathiocresol, dithiothreitol and the like. Preferably, mercaptoethanol and dithiothreitol are used. An excess thiol compound can be removed by dialysis, gel filtration and the like. Other than thiol compound, electrolysis, sodium tetrahydroborate, lithium aluminum hydride, sulfite and the like may be used.

The above-mentioned reduction treatment is conducted as appropriate by a known process depending on the kind of reducing agent. For example, when mercaptoethanol or dithiothreitol is used, this reagent is added to FK228 and reacted at room temperature—under heating for 15 min— overnight, preferably at room temperature overnight (see Bio-chemical Experiment Method 8, chemical modification of SH group, Masatsune Ishiguro, Japan Scientific Societies Press, IV, chemical modification of disulfide bond; Biochemical Experiment Method 10, quantitative determination of SH group, Hiroshi Matsumoto, Toyo Kuninori, Japan Scientific Societies Press, III, reduction of SS bond, and the like).

A compound to be the starting material of FK 228 thiol form of the present invention, namely, FK228 or a salt thereof, is a known substance and available. For example, FR901228 substance, which is one of the stereoisomers of FK228, can be obtained by culturing a bacterial strain belonging to the genus *Chromobacterium*, which is capable of production thereof, under aerobic conditions and recovering the substance from culture broth. The bacterial strain belonging to the genus *Chromobacterium*, which is capable of producing FR901228 substance, is, for example, *Chromobacterium violaceum* WB968 strain (FERM BP-1968). The FR901228 substance can be obtained from this production strain according to JP-B-7-64872. The FR901228 substance is preferably recovered from a bacterial strain belonging to the genus *Chromobacterium*, which is capable of producing FR901228 substance, because it can be obtained more easily. In addition, a synthesized or semi-synthesized FR901228 substance is also advantageous because further purification step is unnecessary or less. Alternatively, FK228 can be semi-synthesized or completely synthesized according to a method conventionally known. More specifically, the method reported by Khan W. Li, et al. (J. Am. Chem. Soc., vol. 118, 7237–7238 (1996)) can be used.

Another aspect of the FK228 thiol form of the present invention is a compound wherein $R^1$ and/or $R^2$ are/is a thiol-protecting group. This compound can be prepared by introducing a thiol-protecting group into the compound of the present invention wherein $R^1$ and $R^2$ are hydrogen atoms.

A suitable agent for introducing thiol-protecting group to be used in this reaction is appropriately determined depending on the protecting group to be introduced. For example, those generally used, such as chloride of the corresponding protecting group (e.g., benzyl chloride, methoxybenzyl chloride, acetoxybenzyl chloride, nitrobenzyl chloride, picolyl chloride, picolyl chloride-N-oxide, anthryl methyl chloride, isobutoxymethyl chloride, phenylthiomethyl chloride etc.) and alcohols of the corresponding protecting group (diphenylmethyl alcohol, adamanthyl alcohol, acetamidemethyl alcohol, benzamidomethyl alcohol etc.), dinitrophenyl, isobutylene, dimethoxymethane, dihydropyran, t-butyl chloroformate and the like can be mentioned.

This reaction can be carried out according to a conventionally known method for a protecting group-introducing agent or a suitable combination of such methods. The deprotection of the protecting group is also known to those of ordinary skill in the art (PROTECTIVE GROUPS IN ORGANIC SYNTHESIS, Second Edition, T. W. Greene, P. G. M. Wuts WILEY-INTERSCIENCE). As one specific example, when the introducing agent is benzyl chloride, protection of the thiol group is achieved by reaction in the presence of 2N sodium hydroxide and ethanol at 25° C. for 30 min, and deprotection thereof is achieved by treatment in the presence of sodium and ammonia for 10 min.

FK228 thiol form of the present invention has a potent histone deacetylase inhibitory activity, and is useful as a histone deacetylase inhibitor in various mammals inclusive of human, such as monkey, mouse, rat, rabbit, swine, dog, horse, cow and the like.

Moreover, because of its histone deacetylase inhibitory activity, a pharmaceutical composition containing the FK228 thiol form of the present invention is useful as an agent for the treatment or prophylaxis of the diseases (e.g., inflammatory disorder, diabetes, diabetic complication, homozygous thalassemia, fibrosis, cirrhosis, acute promyelocytic leukemia (APL), protozoiasis and the like) induced by abnormal gene expression. In addition, the pharmaceutical composition of the present invention is useful as an antitumor agent and immunosuppressant which prevents rejection of organ transplant and autoimmune diseases exemplified below. To be specific, the following diseases are targeted.

Rejection reactions by transplantation of organs or tissues such as the heart, kidney, liver, bone marrow, skin, cornea, lung, pancreas, small intestine, limb, muscle, nerve, intervertebral disc, trachea, myoblast, cartilage, etc.;

graft-versus-host reactions following bone marrow transplantation;

autoimmune diseases such as rheumatoid arthritis, systemic lupus erythematosus, Hashimoto's thyroiditis, multiple sclerosis, myasthenia gravis, type I diabetes, etc.;

infections caused by pathogenic microorganisms (e.g., *Aspergillus fumigatus, Fusarium oxysporum, Trichophyton asteroides*, etc.);

inflammatory or hyperproliferative skin diseases or cutaneous manifestations of immunologically-mediated diseases (e.g., psoriasis, atopic dermatitis, contact dermatitis, eczematoid dermatitis, seborrheic dermatitis, lichen planus, pemphigus, bullous pemphigoid, epidermolysis bullosa, urticaria, angioedema, vasculitides, erythema, dermal eosinophilia, lupus erythematosus, acne, and alopecia areata);

autoimmune diseases of the eye (e.g., keratoconjunctivitis, vernal conjunctivitis, uveitis associated with Behcet's disease, keratitis, herpetic keratitis, conical keratitis, corneal epithelial dystrophy, keratoleukoma, ocular premphigus, Mooren's ulcer, scleritis, Graves' ophthalmopathy, Vogt-Koyanagi-Harada syndrome, keratoconjunctivitis sicca (dry eye), phlyctenule, iridocyclitis, sarcoidosis, endocrine ophthalmopathy, etc.);

reversible obstructive airways diseases [asthma (e.g., bronchial asthma, allergic asthma, intrinsic asthma, extrinsic asthma, and dust asthma), particularly chronic or inveterate asthma (e.g., late asthma and airway hyper-responsiveness), bronchitis, etc.];

mucosal or vascular inflammations (e.g., gastric ulcer, ischemic or thrombotic vascular injury, ischemic bowel diseases, enteritis, necrotizing enterocolitis, intestinal damages associated with thermal burns, leukotriene B4-mediated diseases);

intestinal inflammations/allergies (e.g., coeliac diseases, proctitis, eosinophilic gastroenteritis, mastocytosis, Crohn's disease and ulcerative colitis);

food-related allergic diseases with symptomatic manifestation remote from the gastrointestinal tract (e.g., migrain, rhinitis and eczema);

renal diseases (e.g., intestitial nephritis, Goodpasture's syndrome, hemolytic uremic syndrome, and diabetic nephropathy);

nervous diseases (e.g., multiple myositis, Guillain-Barre syndrome, Meniere's disease, multiple neuritis, solitary neuritis, cerebral infarction, Alzheimer's disease, Parkinson's disease, amyotrophic lateral sclerosis (ALS), and radiculopathy);

cerebral ischemic diseases (e.g., head injury, hemorrhage in brain (e.g., subarachnoid hemorrhage, intracerebral hemorrhage), cerebral thrombosis, cerebral embolism, cardiac arrest, stroke, transient ischemic attack (TIA), and hypertensive encephalopathy);

endocrine diseases (e.g., hyperthyroidism, and Basedow's disease);

hematic diseases (e.g., pure red cell aplasia, aplastic anemia, hypoplastic anemia, idiopathic thrombocytopenic purpura, autoimmune hemolytic anemia, agranulocytosis, pernicious anemia, megaloblastic anemia, and anerythroplasia);

bone diseases (e.g., osteoporosis);

respiratory diseases (e.g., sarcoidosis, pulmonary fibrosis, and idiopathic interstitial pneumonia);

skin diseases (e.g., dermatomyositis, leukoderma vulgaris, ichthyosis vulgaris, photosensitivity, and cutaneous T-cell lymphoma);

circulatory diseases (e.g., arteriosclerosis, atherosclerosis, aortitis syndrome, polyarteritis nodosa, and myocardosis);

collagen diseases (e.g., scleroderma, Wegener's granuloma, and Sjögren's syndrome);

adiposis;

eosinophilic fasciitis;

periodontal diseases (e.g., damage to gingiva, periodontium, alveolar bone or substantia ossea dentis);

nephrotic syndrome (e.g., glomerulonephritis);

male pattern alopecia, alopecia senile;

muscular dystrophy;

pyoderma and Sezary syndrome;

chromosome abnormality-associated diseases (e.g., Down's syndrome);

Addison's disease;

active oxygen-mediated diseases [e.g., organ injury (e.g., ischemic circulation disorders of organs (e.g., heart, liver, kidney, digestive tract, etc.) associated with preservation, transplantation, or ischemic diseases (e.g., thrombosis, cardial infarction, etc.));

intestinal diseases (e.g., endotoxin shock, pseudomembranous colitis, and drug- or radiation-induced colitis);

renal diseases (e.g., ischemic acute renal insufficiency, chronic renal failure);

pulmonary diseases (e.g., toxicosis caused by pulmonary oxygen or drugs (e.g., paracort, bleomycin, etc.), lung cancer, and pulmonary emphysema);

ocular diseases (e.g., cataracta, iron-storage disease (siderosis bulbi), retinitis, pigmentosa, senile plaques, vitreous scarring, corneal alkali burn);

dermatitis (e.g., erythema multiforme, linear immunoglobulin A bullous dermatitis, cement dermatitis);

and other diseases (e.g., gingivitis, periodontitis, sepsis, pancreatitis, and diseases caused by environmental pollution (e.g., air pollution), aging, carcinogen, metastasis of carcinoma, and hypobaropathy)];

diseases caused by histamine release or leukotriene C4 release;

restenosis of coronary artery following angioplasty and prevention of postsurgical adhesions;

Autoimmune diseases and inflammatory conditions (e.g., primary mucosal edema, autoimmune atrophic gastritis, premature menopause, male sterility, juvenile diabetes mellitus, pemphigus vulgaris, pemphigoid, sympathetic ophthalmitis, lens-induced uveitis, idiopathic leukopenia, active chronic hepatitis, idiopathic cirrhosis, discoid lupus erythematosus, autoimmune orchitis, arthritis (e.g., arthritis deformans), or polychondritis);

Human Immunodeficiency Virus (HIV) infection, AIDS;

allergic conjunctivitis;

hypertrophic cicatrix and keloid due to trauma, burn, or surgery.

Moreover, the FK228 thiol form of the present invention is useful as an expression potentiator or reactivation promoter of a transgene due to its histone deacetylase inhibitory activity.

In the present invention, potentiation of the expression of a transgene means potentiation in the host cell of the expression of an exogenous gene transduced by genetic engineering into the cells of human and various animals (e.g., mouse, rat, swine, dog, horse, cow and the like). The potentiation of the expression of the transgene may be at the cell level (i.e., in vitro) or at an individual level (i.e., in vivo), with preference given to that in vivo.

As used herein, in vivo and in vitro means as these terms are used in this field. That is, "in vivo" means that the target biological functions and responses are expressed within tissues of the living body, and "in vitro" means that such functions and responses are expressed in a test tube (tissue culture system, cell culture system, non-cell system and the like).

In the present invention, reactivation of a transgene means release of the suppression of the expression (silencing) of an exogenous gene transduced by genetic engineering into the cells of human and various animals (e.g., mouse, rat, swine, dog, horse, cow and the like), and the present invention can promote the reactivation. Besides the release of silencing, the present invention can promote transcription activity of a transgene that shows stable expression at a constant level, and potentiate the expression. Such effect is also encompassed in the "reactivation of the transgene" of the present invention. The promotion of the reactivation of the transgene may be at a cell level (i.e., in vitro) or at an individual level (i.e., in vivo), with preference given to that in vivo.

An exogenous gene can be transduced by a method known in the pertinent field. For example, transfer of DNA by physical method (microinjection method, electroporation method and the like), transfer of DNA by chemical method (calcium phosphate method, DEAE-dextran method etc.), biological method (virus vector such as retrovirus and adenovirus, and the like), new methods such as HVJ-liposome method and the like can be beneficially used.

When the FK228 thiol form of the present invention or a salt thereof is used as a pharmaceutical agent, it can be used as a solid, semi-solid or liquid pharmaceutical preparation containing FK228 thiol form or a salt thereof as an active ingredient in admixture with an organic or inorganic carrier or excipient suitable for oral or parenteral application. The active ingredient can be admixed with a typical, non-toxic pharmaceutically acceptable carrier suitable for the dosage form, such as powder, tablet, pellet, capsule, suppository, liquid, emulsion, suspension, aerosol, spray and other form for use. Where necessary, auxiliary agent, stabilizer, tackifier and the like may be used. These carriers and excipients may be sterilized where necessary, or a sterilization treatment may be applied after formulation into a preparation. FK228 thiol form or a salt thereof are contained in the expression potentiator or reactivation promoter in an amount sufficient to produce a desired effect on the condition that requires potentiation of the expression of a transgene or reactivation thereof. In particular, when the inventive expression potentiator and reactivation promoter of a transgene is used for a gene therapy, parenteral administration is preferable, namely, intravenous administration, intramuscular administration, direct administration into the tissue, intra-nostril cavity administration, intradermal administration, administration into cerebrospinal fluid, administration into biliary tract, intravaginal administration and the like. In addition, a liposome method capable of direct administration to the site and organ where-expression and reactivation of a transgene are requested, and the like can be preferably used.

The therapeutically effective amount of the active ingredient FK228 thiol form and a salt thereof varies and is determined depending on the age and condition of individual patient to be treated, and when it is used as an expression potentiator or a reactivation promoter of a transgene, on the kind of the transgene, and the kind of a disease where potentiation of the expression and promotion of reactivation of a transgene are requested.

The administration method of a pharmaceutical agent containing the FK228 thiol form of the present invention or a salt thereof as an active ingredient is free of any particular limitation as long as it can provide the desired effect, and, for example, the agent can be administered orally or parenterally once a day or several times a day. When it is used for a gene therapy, the administration route most suitable for the expression and reactivation of the transgene is appropriately selected in consideration of the specific nature of use. For example, when it is used for a gene therapy of tumor, direct administration to the tumor cell (e.g., liposome method) is preferable.

The expression potentiator and reactivation promoter of a transgene of the present invention is characterized by the potentiation of the expression of a transgene, as well as release of the suppression of the transgene expression, wherein the interaction with the transgene is an important factor for the exertion of the effect. Therefore, the timing of the administration of the transgene and the administration (in vivo, in vitro) to the subject of the expression potentiator or reactivation promoter of the present invention are appropriately determined according to the desired effect. When the potentiation of the expression of a transgene is aimed, for example, the inventive transgene expression potentiator is preferably administered along with or after the administration of the transgene. When the promotion of the reactivation of a gene already transduced is aimed, the inventive transgene reactivation promoter is preferably administered when the reactivation is needed after the administration of the transgene. When the expression potentiator or reactivation promoter of a transgene of the present invention is to be administered after the administration of the transgene, the timing of the administration is appropriately determined according to the desired effect and its level, and state of expression of the gene previously transduced (level of expression, position of the transgene and the like).

In particular, the expression potentiator and reactivation promoter of a transgene of the present invention can be beneficially applied to a gene therapy. For the gene therapy of cancer, for example, transfer of a suicide gene, DNA vaccine and the like can be applied. As the transfer of a suicide gene, there is exemplified transfer of cytosine deaminase (enzyme to convert an anticancer agent, 5-fluorocytosine (5-FC) from an inactive type to an active type compound) gene into cancer cells. The expression of this gene in a cancer cell can be potentiated by the present invention (induction of anti-tumor effect by cancer cell-specific and efficient conversion of 5-FC to an active type 5-FC). As the DNA vaccine, there is exemplified a tumor-associated antigen gene specifically expressed in a cancer cell. Transfer of the gene to a cancer patient, or reactivation of an endogenous tumor-associated antigen gene, expression of which is suppressed, or both of them, provide potentiation of the expression of the function of the tumor-associated antigen gene, which in turn enhances the immunity to the cancer of the patient.

In a gene therapy of cancer, p53 gene, cytokine gene (e.g., IL2, IL12 gene), antisense gene (K-ras antisense) and the like are also used. For the gene therapy of cystic fibrosis, CFTR gene can be used and for the gene therapy of hemophilia, a coagulant factor gene can be used.

EXAMPLES

The present invention is explained in more detail in the following by way of Examples. It is needless to say that the present invention is not limited by these examples.

Production Example

Production of FR135313

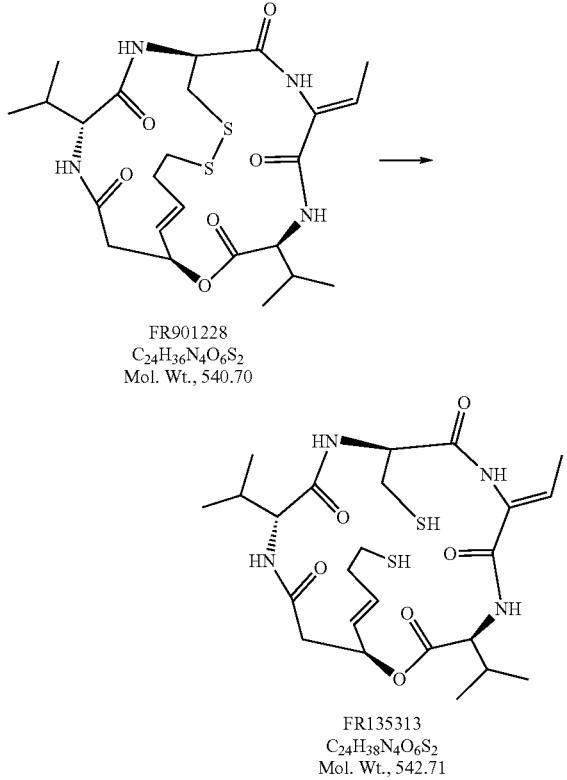

FR901228
$C_{24}H_{36}N_4O_6S_2$
Mol. Wt., 540.70

FR135313
$C_{24}H_{38}N_4O_6S_2$
Mol. Wt., 542.71

FR901228 isolated and purified according to the description of JP-B-7-64872 was used as a starting substance. To a mixture of FR901228 (51.6 mg, 95 μmol), water (40 ml) and acetonitrile (10 ml), was added dithiothreitol (412 mg, 2.66 mmol), and the mixture was left standing overnight at room temperature. Acetonitrile was distilled away and the mixture was purified by preparative HPLC (washing was conducted using aqueous solution of 20% acetonitrile/0.05% trifluoroacetic acid and elution was conducted using an aqueous solution of 50% acetonitrile/0.05% trifluoroacetic acid).

The fractions containing the objective compound were recovered and lyophilized to give FR135313 as a powder (14.8 mg, yield 28.7%)

$^1$H-NMR(500 MHz, DMF-$d_7$) δ:9.35 (1H, br s, exchangeable), 8.15 (1H, br d, J=9 Hz, exchangeable), 8.01 (1H, br d, J=7 Hz, exchangeable), 6.83 (1H, d, J=7 Hz, exchangeable), 6.81 (1H, q, J=7 Hz), 5.72 (1H, m), 5.61–5.54 (2H, m), 4.60(1H, dd, J=10 Hz, 5 Hz), 4.55 (1H, m), 4.15 (1H, dd, J=9 Hz, 8 Hz), 2.97–2.88 (2H, m), 2.73–2.63 (2H, m), 2.55 (2H, m), 2.44 (1H, t, J=8 Hz, exchangeable), 2.34–2.27 (3H, m), 2.20 (1H, m), 2.08 (1H, t, J=8 Hz, exchangeable), 1.72 (3H, d, J=7 Hz), 0.98 (3H, d, J=7 Hz), 0.95 (3H, d, J=7 Hz), 0.88 (3H, d, J=7 Hz), 0.87 (3H, d, J=7 Hz) MS m/e 654 (M+TFA)

The purity of the objective compound was confirmed by HPLC under the following conditions.

HPLC Conditions column: YMC-PACK ProC18 (YMC Co., Ltd), 4.6×150 mm elution: aqueous solution of 50% acetonitrile/0.05% trifluoroacetic acid flow rate: 1 ml/min detection : 214 nm, 254 nm retention time: 4.01 min (retention time of starting substance FR901228 substance is 4.27 min)

Experimental Example

Assay of Histone Deacetylase Activity

The histone deacetylase inhibitory activity of the FR135313 substance synthesized in Production Example 1 was examined.

1. Test material·Test method (1) Cell

Mouse breast cancer FM3A was supplied by Dr. Dai Ayusawa of Medical Department, Yokohama City University. This cell was subcultured in an ES medium containing 2% FBS (Flow Laboratories, hereinafter to be referred to as ES medium) at 37° C., in 5% $CO_2$.

(2) Pharmaceutical Agent

Sodium butyrate was purchased from Waco Pure Chemical Industries, Ltd. and [$^3$H] sodium acetate was purchased from Amersham.

(3) Buffer and the Like

Lysis buffer (pH 6.5): 10 mM Tris-HCl (Sigma), 50 mM sodium bisulfite (Nakarai Chemical, Ltd), 1% Triton X-100 (Nakarai Chemical, Ltd), 10 mM magnesium chloride (Nakarai Chemical, Ltd), 8.6% sucrose (Nakarai Chemical, Ltd)

Washing buffer (pH 7.4): 10 mM Tris-HCl, 13 mM EDTA (Sigma)

HDA buffer (pH 7.5): 15 mM potassium phosphate (Nakarai Chemical, Ltd), 5% glycerol, 0.2 mM EDTA (4) Preparation of [³H] Acetylated Histone The [³H] acetylated histone to be the substrate of histone deacetylase was prepared by culturing 1×10⁸ cells of FM3A cell (suspended in 50 ml of ES medium) in the presence of 0.5 mCi/ml [³H] sodium acetate and 5 mM sodium butyrate at 37° C. in 5% $CO_2$ for 30 min, and immediately extracting histone fraction from the treated cells according to the following method. The specific radioactivity was 0.45 μCi/mg histone.

(5) Extraction of Histone Protein from Cell

Extraction of histone protein from culture cell was conducted according to the method of Yoshida et al. (M. Yoshida et al., J. Biol. Chem. 265, 17174–17179 (1990)). 1×10⁸ cells of FM3A cells labeled with [³H] sodium acetate were recovered and washed once with PBS. The washed cells were suspended in 1 ml of ice-cooled lysis buffer and ruptured by Dounce homoegnizer. The nucleus was collected by centrifugation at 1000 rpm for 10 min, and washed 3 times with the lysis buffer and then once with the washing buffer. The residue was suspended in 0.1 ml of ice-cooled distilled water and concentrated sulfuric acid (Waco Pure Chemical Industries, Ltd.) was added to the final concentration of 0.4 N, and the mixture was stood at 4° C. for 1 hr. The suspension was centrifuged in a microcentrifugal machine at 15,000 rpm for 5 min, the supernatant was recovered, to which 1 ml of acetone was added, and the supernatant was left standing overnight at −20° C. The precipitate was recovered by centrifugation in a microcentrifugal machine at 15,000 rpm for 10 min, and dried.

(6) Extraction of Crude Histone Deacetylase from Cell

Mouse histone deacetylase was pre-purified from FM3A cells. Suspended cultured FM3A cells (concentration of 1×10⁶ cells/ml in ES medium 4L) in an 8L spinner flask were recovered by centrifugation and suspended in 40 ml of HDA buffer. The cells were ruptured by a Dounce homoegnizer, and cell nucleus was recovered by centrifugation at 35,000×g for 10 min and further ruptured in 20 ml of 1 M ammonium sulfate solution. A cloudy rupture suspension was ultrasonicated and centrifuged to give a transparent extract, to which ammonium sulfate was added and the ammonium sulfate concentration was raised to 3.5 M, whereby histone deacetylase precipitated. The precipitate was dissolved in 10 ml of HDA buffer, and dialyzed against 4 L of the same buffer. The dialysate was buffered with HDA buffer. It was applied to DEAE-cellulose (DE52, 25×85 mm, Whatman) and eluted with 300 ml of NaCl by linear gradient (0–0.6 M). The histone deacetylase activity was eluted as a single peak activity in 0.2–0.3 M NaCl elution fraction. As a result, histone deacetylase was purified to about 60 times specific activity.

(7) in Vitro Histone Acetylation Reaction

4 μl of [³H] acetylated histone (2500 cpm/5 μg) and 96 μl of crude histone deacetylase fraction were admixed. An ethanol solution (1 μl) of FR135313 substance prepared according to the above-mentioned Production Example was added to the mixture at various final concentrations, and the mixture was reacted at 37° C. for 10 min. The reaction was terminated by the addition of 10 μl of concentrated hydrochloric acid, and released [³H] acetic acid was extracted with 1 ml of ethyl acetate, from which 0.9 ml was added to 5 ml of toluene scintillation solution and the radioactivity was measured.

(8) Result

The FR135313 substance, which is in a reduced form (thiol form), showed histone deacetylase inhibitory activity as shown in $IC_{50}$ value of not more than 1 ng/ml.

The thiol group showed a strong chelating action and therefore, the FR901228 substance that became a thiol form under the reduction environment, is considered to inhibit the activity of histone deacetylase by its directivity to this enzyme, which is a metalloenzyme.

INDUSTRIAL APPLICABILITY

The compound of the formula (I), which is a reduced form (thiol form) of FK228, particularly FR135313 substance, which is a reduced form (thiol form) of FR901228 substance, and salts thereof have a strong histone deacetylase inhibitory activity, and are useful as a histone deacetylase inhibitor or an agent for the prophylaxis or treatment of inflammatory disorder, diabetes, diabetic complication, homozygous thalassemia, fibrosis, cirrhosis, acute promyelocytic leukemia (APL), organ transplant rejection or autoimmune disease, and further as an expression potentiator or reactivation promoter of a transgene.

By controlling the activity of thiol group, the histone deacetylase inhibitory activity can be controlled, thereby enabling development of a pharmaceutical agent suitable for various clinical applications.

What is claimed is:

1. A compound represented by the formula (I)

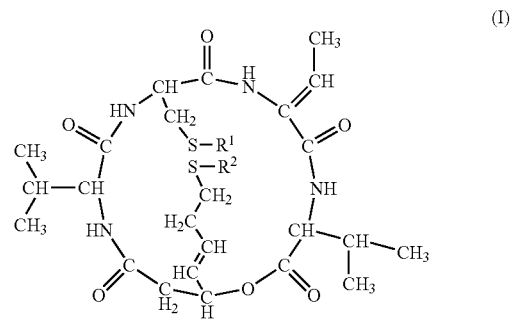

wherein $R^1$ and $R^2$ are the same or different and each is a hydrogen atom or a thiol-protecting group, or a salt thereof.

2. The compound of claim 1, wherein $R^1$ and $R^2$ are each a hydrogen atom, or a salt thereof.

3. The compound of claim 2, which is represented by the formula (II)

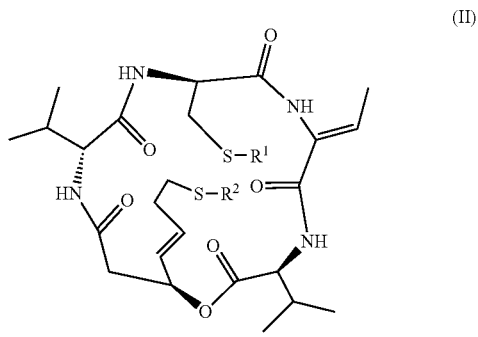

wherein $R^1$ and $R^2$ are each a hydrogen atom, or a salt thereof.

4. A method of producing a compound of claim 1 or a salt thereof, which comprises cleaving a disulfide bond in a compound represented by the formula (III)

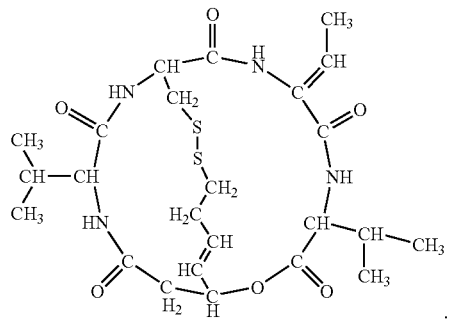

(III)

5. The method of claim 4, wherein the compound of the formula (III) is represented by the formula (IV)

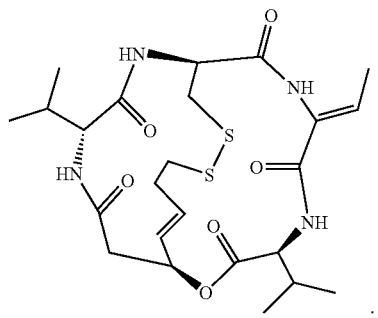

(IV)

6. A method for the treatment of tumor, inflammatory disorders, diabetes, diabetic complication, homozygous thalassemia, fibrosis, cirrhosis, acute promyelocytic leukemia (APL), organ transplant rejection or autoimmune disease, which comprises administering a pharmaceutically effective amount of a compound of claim 1, or a salt thereof, to a patient in need thereof.

* * * * *